(12) United States Patent
Rauch et al.

(10) Patent No.: US 8,877,514 B2
(45) Date of Patent: Nov. 4, 2014

(54) AQUEOUS SOLUTION FOR USE AS MEDIUM FOR THE SPECIFIC BINDING REACTION OF A BINDING PAIR

(75) Inventors: Peter Rauch, Weiβensberg (DE); Tobias Polifke, Hergensweiler (DE); Angela Zellmer, Vogt (DE)

(73) Assignee: Candor Bioscience GmbH, Weissensberg (DE)

( * ) Notice: Subject to any disclaimer, the term of this patent is extended or adjusted under 35 U.S.C. 154(b) by 1758 days.

(21) Appl. No.: 10/590,686

(22) PCT Filed: Feb. 26, 2004

(86) PCT No.: PCT/EP2004/050209
§ 371 (c)(1),
(2), (4) Date: Jun. 15, 2007

(87) PCT Pub. No.: WO2005/083433
PCT Pub. Date: Sep. 9, 2005

(65) Prior Publication Data
US 2008/0064116 A1 Mar. 13, 2008

(51) Int. Cl.
*G01N 33/53* (2006.01)

(52) U.S. Cl.
CPC ............ *G01N 33/5306* (2013.01); *G01N 33/53* (2013.01); *Y10S 435/962* (2013.01)
USPC ............................. 436/501; 435/7.1; 435/962

(58) Field of Classification Search
CPC ... G01N 33/50; G01N 33/53; G01N 33/5306; Y10S 425/962
See application file for complete search history.

(56) References Cited

U.S. PATENT DOCUMENTS

| 4,485,177 A * | 11/1984 | Siedel et al. ............... 530/389.8 |
| 4,931,385 A | 6/1990 | Block et al. |
| 5,616,460 A | 4/1997 | Figard |
| 6,503,702 B1 * | 1/2003 | Stewart .............................. 435/5 |

FOREIGN PATENT DOCUMENTS

| DE | 41 04 128 A1 | 3/1992 |
| GB | 2 062 224 A | 5/1981 |
| JP | 10-245400 | 9/1998 |

OTHER PUBLICATIONS

Kaplan et al. When is a heterophile antibody not a heterophile antibody? When it is an antibody against a specific immunogen. Clinical Chemistry 1999, vol. 45, No. 5, pp. 616-618.*
Sigma-Aldrich. Non-ionic Detergents. Sigma-Aldrich Co. LLC. 2014, pp. 1-10.*
Ezan, E. et al. (1989) "Triton X-100 eliminates plasma proteins interference in a radioimmunoassay for luteinizing hormone-releasing hormone (LHRH) and LHRH analogues" Journal of Immunological Methods 122:291-296.
Holownia, P. et al. (2001) "Effect of poly(ethylene glycol), tetramethylammonium hydroxide, and other surfactants on enhancing performance in a latex particle immunoassay of c-reactive protein" Anal. Chem. 73:3426-3431.
Notice of Rejection in Japanese Patent Application No. 2007-500065 dated Sep. 29, 2009. The Notice cites JP 10-245400.
Preissner, M. et al. 2005 "Prevalence of heterophilic antibody interferences in eight automated tumor marker immunoassays" *Clinical Chemistry* 51: 208-210.

* cited by examiner

*Primary Examiner* — Shafiqul Haq
(74) *Attorney, Agent, or Firm* — Knobbe, Martens, Olson & Bear, LLP

(57) ABSTRACT

The present invention refers to an aqueous solution for use as medium for the specific binding reaction of a binding pair, wherein a first binding member recognizes its complementary second binding member. The solution contains a) a buffer to control pH; b) a compound A selected from a compound defined by the general formula I $R^1-[[CR^2R^3]_P-O]_q-R^4$, wherein $R^1$ is hydrogen or hydroxy group, $R^2$ for each unit independently is hydrogen or hydroxy group, $R^3$ is hydrogen, methyl group, or ethyl group, $R^4$ is hydrogen or alkyl group, p is an integer of from 2 to 10 and q is an integer of from 1 to 100, with the proviso that the compound at least carries two hydroxy groups; a polyol; or saccharide; and c) a non-ionic detergent.

17 Claims, 2 Drawing Sheets

AQUEOUS SOLUTION FOR USE AS MEDIUM FOR THE SPECIFIC BINDING REACTION OF A BINDING PAIR

RELATED APPLICATIONS

This application is a U.S. National Phase of International Application No.: PCT/EP2004/050209, filed Feb. 26, 2004 designating the U.S. and published in English on Sep. 9, 2005 as WO 2005/083433.

FIELD OF THE INVENTION

The present invention relates to an aqueous solution for the use as medium for the specific binding reaction of a binding pair.

BACKGROUND OF THE INVENTION

Immunoassays where one or more antibodies are used to detect the test substance (analyte) in a test sample are widely known. The evolution of immunoassay methods increased the sensitivity of this test. Despite of the developments within the recent decades, there remains a desire to eliminate unspecific binding reactions, cross-reactivities and the influence of the compounds present in the matrix.

Immunoassays depend upon the ability of a first binding member of a binding member pair, e.g. an antigen or a ligand, to specifically bind to a second binding member of a binding member pair, e.g. an antibody or a receptor. In order to determine the extend of such binding, a conjugate, comprising one of such binding members are labeled with a detectable moiety. Such binding member pairs can be an antigen and an antibody directed to such an antigen.

Immunoassays can be performed in a competitive immunoassay format or in a sandwich immunoassay format. In the competitive immunoassay format an antigen can be immobilized to a solid phase material whereby the amount of detectable moiety that is bound to a solid phase material can be detected, measured and correlated to the amount of antibody present in the test sample. Examples of solid phase materials include beads, particles, micro-particles and the like. In the sandwich immunoassay format a test sample, containing for example an antibody, is contacted with a protein such as an antigen. The antigen is immobilized on a solid phase material. Examples of solid phase materials include beads, particles, micro-particles and the like. The solid phase material is typically created with a second antigen or antibody that has been labeled with a detectable moiety. The second antigen or antibody, respectively, then becomes bound to the corresponding antibody or antigen, respectively, on the solid phase material and, after one or more washing steps, to remove any unbound material an indicator material such as a chromogenic substance, is introduced to react with the detectable moiety to produce the detectable signal. e.g. a color change. The color change is then detected, measured and correlated to the amount of antibody present in the test sample. It should also be noted that various dilutents and buffers are also required to optimize the operation of the micro-particles, antigens, conjugates and other components of the assay that participate in chemical reactions.

In order to achieve optimal results in immunoassays the solution which is used for the binding reactions between the binding partners (for example the antibody and antigen reaction or the complex formation of ligand and receptor) must provide a medium that optimizes the ability of antibodies to bind to the antigen, or must provide a medium that optimizes the ability of ligands to bind to the receptor, while non-specific interactions, low-affinity binding and matrix effects are strongly reduced or even prevented in order to avoid the generation of a false signal.

In order to eliminate non-specific interactions and cross-reactivities detergents have been added to buffers which are used for washing steps after the binding reaction in order to remove unspecific bindings.

For immunoassays, like western-blot analyses, enzyme-linked immuno-sorbant assay (ELISA) and others, solutions containing phosphate buffered saline (PBS) supplemented with bovine serum albumin and 0.01 to 0.05 (v/v) Tween® 20 is used as medium for the binding reactions between the binding partners (for example antibody and antigen). It is, however, very often experienced that unspecific or low-affinity binding, cross-reactivities and matrix effects can not be avoided with such buffers of the state of art. For example, when developing a CRP-assay involving the detection of a plurality of analytes it appeared that cross-reactivities due to the use of the plurality of antibodies as well as matrix effects became a problem, which could not be solved by the use of conventional immunoassay buffers.

The object of the present invention therefore was to provide a solution for the use as a medium for the specific binding reaction of a binding member pair wherein the unspecific binding, low affinity binding, cross-reactivities and matrix effects are strongly reduced or even prevented. Furthermore, it was the object of the present invention to provide a method of an immunoassay, wherein unspecific and low affinity binding, cross-reactivities and matrix effects are reduced or prevented.

SUMMARY OF THE INVENTION

The object of the present invention is solved by an aqueous solution for use as medium for the specific binding reaction of a binding member pair, wherein a first binding member recognizes its complementary second binding member, the solution comprising
  a) a buffer to control pH;
  b) a compound A selected from the group consisting of:
    a compound defined by the general formula I $R^1$—$[[CR^2R^3]_p$—$O]_q$—$R^4$, wherein $R^1$ is hydrogen or hydroxy group, $R^2$ for each unit independently is hydrogen or hydroxy group, $R^3$ is hydrogen, methyl group, ethyl group, $R^4$ is hydrogen or alkyl group, p is an integer of from 2 to 10 and q is an integer of from 1 to 100, with the proviso that the compound at least carries two hydroxy groups;
    polyol;
    saccharide;
  c) a non-ionic detergent.

In case $R^4$ in the general formula I of compound A is hydrogen the neighbouring residue $R^2$ is also hydrogen. In case $R^1$ is hydroxy group the neighbouring residue $R^2$ is hydrogen. In a preferred embodiment q in the formula of compound A is an integer of from 1 to 50, more preferred from 1 to 30.

The inventors of the present invention surprisingly have found that the aqueous solution according to the present invention reduces the cross-reactivities, matrix effects, unspecific bindings and low affinity-binding in immunoassays. Furthermore, it was found that even effects due to heterophilic antibodies (human anti-mouse-antibody) are prevented when the aqueous solution according to the present invention is used. Additionally, negative effects due to rheuma factors, hemoglobin, bilirubin and triglycerides can be avoided with this buffer even in case of plasma applications.

As used herein a "binding member pair" comprises a "first binding member" and a "second binding member". Both binding members undergo a specific binding to each other. The first binding member of a binding member pair may be an antigen or a ligand, respectively. The second binding member (e.g. an antibody or a receptor, respectively) specifically recognizes and binds to the first binding member (e.g. antigen or ligand, respectively). The second binding member is the corresponding binding member and therefore also named "corresponding binding member". The artisan will understand that the terms "first" binding member and "second" binding member, respectively, may be for example the antigen and the corresponding antibody, respectively, or vice versa.

The aqueous solution according to the present invention represents a universal buffer as a medium in immunoassays and binding reactions in a variety of matrices, for example blood plasma, blood serum and others. In case of multi-analyte applications, for example, if protein chips are used, the simultaneous incubation of several (or a plurality) of analytes and several antibodies, unspecific bindings and cross-reactivities very often occur. Such undesired binding reactions have been observed in many cases. The use of standard ELISA buffers known in the state of art could not prevent such cross-reactivity effects. In addition in the state of art, the use of native samples resulted in matrix effects which gave erroneous measurements compared to other methods for reference. As used herein the term "matrix" refers to all compounds present in a native sample, like blood serum; in particular the term "matrix" refers to the organic and especially to biological compounds such as proteins.

The aqueous solution according to the present invention may be used as medium for the binding reaction of a binding pair, as sample dilution buffers for immunoassays and binding reactions as well as dilution buffer for antibodies and antigens, respectively. Further applications are multi-analyte immunoassays and proteomics, wherein undesired cross-reactivities of antibodies labeled with the fluorophor can be prevented. Fluorophor-labled antibodies tend to bind other proteins in an unspecific manner. By using the aqueous solution according to the present invention such effects can be avoided.

By using the buffer according to the present invention in immunoassays like ELISA and protein chips a further positive effect was shown. When incubating the surface carrying the immobilized antibodies with the buffer according to the present invention the activity of the immobilized antibodies was increased. This is resulting in an enhancement of the binding of the analyte to the immobilized antibody. In conclusion, the buffer according to the present invention in addition to the reduction of unspecific signals and unspecific effects also increases the specific signals due to a positive influence on the specific binding reaction between the analyte and the antibody. The resulting increase of the activity of the immobilized antibodies provides a higher sensitivity of the respective assay.

The buffer according to the present invention may be used for immunoassays ELISA, EIA, FIA, lateral-flow-test, protein chips, multi-analyte assays, western blots, dot blots, immunohistochemistry, receptor-ligand-assays and immuno-PCR.

DETAILED DESCRIPTION OF THE INVENTION

Figure 1:
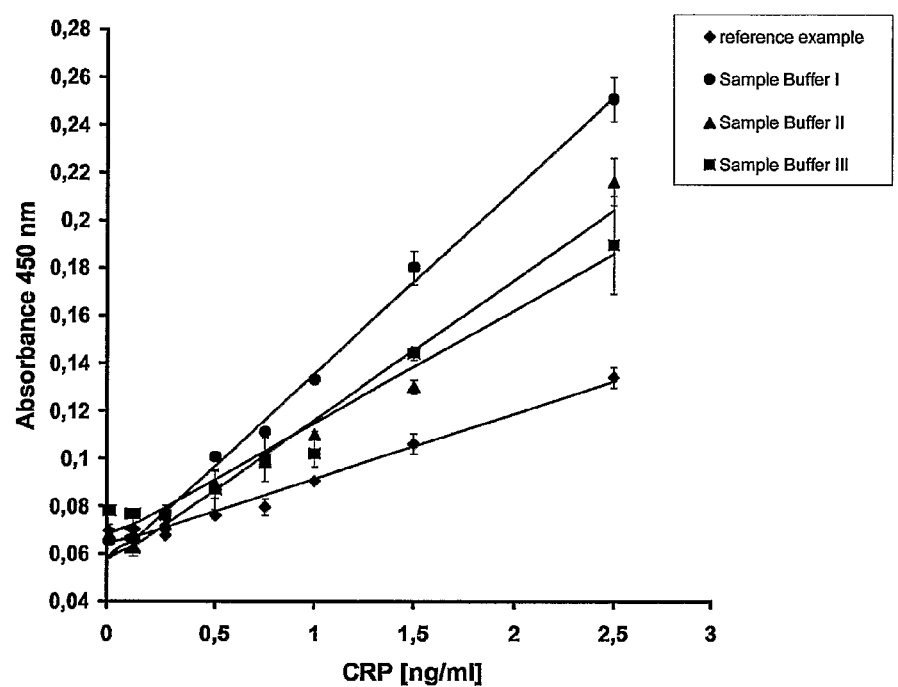
FIG. 1 shows the amount of detector antibody C6 bound to CRP in a sandwich assay as absorbance at 450 nm plotted against the concentration of CRP (ng/ml). The binding reaction of detector antibody C6 to the protein CRP was performed as outlined under Example 1 under standard conditions and by using sample buffers according to the present invention, respectively (see table 1). Sample buffers I to III according to the solution of the present invention reduce the influence of the matrix effects very well. Sample buffer I shows the best sensitivity. The low sensitivity of the reference buffer is caused by a strong matrix effect.

In a preferred embodiment of the present invention the aqueous solution is further comprising a protein in an amount effective to immunologically block non-specific antibody binding. This protein preferably is selected from the group bovine serum albumin, ovalbumin, casein, fetal bovine serum. Further preferred, the protein is present in the aqueous solution in a concentration in the range of 0.1 to 2% (w/v) and further preferred in the range of 0.5 to 1.5% (w/v). These proteins are not recognized by any of the antibodies used in the immunoassays. This unrecognized protein allows the immunological blocking of non-specific antibody-binding by molecules or compounds which might be present in the sample.

In a further embodiment the aqueous solution is comprising a salt selected from the group NaCl, KCl, $NH_4Cl$. Further preferred the aqueous solution is having an ionic strength of 100 mM to 1.5 mM, more preferred of 200 mM to 1 M, even further preferred of 200 mM to 800 mM, particularly more preferred of 200 mM to 600 mM and most preferred of 250 mM to 500 mM. The inventors surprisingly have found that a high ionic strength of the buffer used as a medium for binding reactions, for example, in the range of 200 mM to 600 mM is further reducing unspecific binding and cross-reactivies, while the specific binding reaction is not negatively influenced.

In a particular preferred embodiment the buffer of the aqueous solution is selected from the group Tris (Tris(hydroxymethyl)-aminomethane, Pipes (Piperazine-1,4-bis-2-ethane sulfonic acid), Mes (4-Morpholino ethane sulfonic acid), Hepes (4-(2-hydroxyethyl)-1-piperazine-ethane sulfonic acid), phosphate buffer.

In a further preferred embodiment the compound A is selected from the group polyalkylene glycol, polypropylene glycol, propylene glycol, polyethylene glycol, ethylene glycol, monosaccharides, disaccharides, trisaccharides, saccharose, mannose, trehalose, polyol, glycerol and mixtures thereof. In a preferred embodiment the concentration of the compound A is in the range of 0.5 to 25% (v/v), preferably in the range of 2.0 to 20% (v/v), more preferred in the range of 2.0 to 15% (v/v), further more preferred in the range of 2.0 to 10% (v/v), even more preferred in the range of 2.0 to 7% (v/v), and most preferred around 5% (v/v). The concentration is given in % (v/v) in case coumpound A is a liquid. In case the compound A is solid (for example a saccharide) the concentration has to be understood as % (w/v).

In a further preferred embodiment the aqueous solution comprises as non-ionic detergent a compound of the general formula selected from the group a) a substituted phenyl residue having substituents $R^1$ and $R^2$ ($R^1$-Ph-$R^2$), wherein $R^1$ is $C_1$-$C_9$ alkyl group, and $R^2$ is —O—[$CH_2$—$CH_2$—O]$_a$—H group, wherein "a" is an integer of 5 to 40, wherein $R^2$ in respect to $R^1$ is in para, meta or ortho position.

b

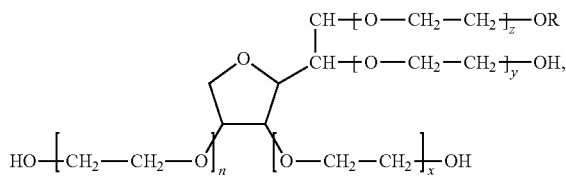

wherein n, x, y and z together is an integer of 5 to 40, R is a fatty acid residue.

Further preferred the non-ionic detergent is selected from the group Dodecylpoly(ethyleneglycolether)$_m$, wherein m is an integer of 5 to 40; 1-O-n-Octyl-β-D-glucopyranoside (n-Octylglucoside); Alkylphenolpoly(ethyleneglycolether)$_m$, wherein m is an integer of 5 to 40, preferably m=11 (Nonidet P40®); 1-O-n-Dodecyl-β-D-glucopyranosyl (1-4) alpha-D-glucopyranoside; Dodecylpoly-(ethyleneglycolether)$_m$, wherein m is an integer of 5 to 40, preferably m=23 (Brij35®); Poly(oxyethylene)(20)-sorbitane mono fatty acid ester, preferably selected from Poly(oxyethylene)(20)-sorbitane monooleate (Tween®80), Poly(oxyethylene)(20)-sorbitane monolaurate (Tween®20), Poly(oxyethylene)(20)-sorbitane monopalmitat (Tween®40), Poly(oxyethylene)(20)-sorbitane monostearate); Octylphenolpoly(ethyleneglycolether)$_m$, wherein m is an integer of 5 to 40, preferably m=10 (Triton®X-100).

In preferred embodiments the concentration of the non-ionic detergent is in the range of 0.1 to 1.0% (v/v). Preferably, the concentration of the non-ionic detergent in the range of 0.15 to 1.0% (v/v), more preferred in the range of 0.2 to 1.0% (v/v), further more preferrred in the range between 0.2 and 0.8% (v/v), even more preferred in the range of 0.25% to 0.6% (v/v), and most preferred about 0.25% (v/v).

An important feature of the present invention is the presence of compound A as given in claim 1 in combination with the non-ionic detergent. Each of said both ingredients (compound A and non-ionic detergent) is present in the aqueous solution of the present invention in higher concentrations as it is known in respect to incubation solutions for immunoassays of the state of art. In a further preferred embodiment an aqueous solution is provided, wherein the ratio of the non-ionic detergent to the compound A is from 1:15 to 1:25, preferably around 1:20.

In a particularly preferred embodiment the aqueous solution comprises compound A in a concentration in the range of 2 to 7% (v/v) and a non-ionic detergent in the range of between 0.2 to 0.8% (v/v). Preferably the aqueous solution is having an ionic strength of 200 mM to 1 M, more preferred of 200 mM to 800 mM, particularly more preferred of 200 mM to 600 mM and most preferred of 250 mM to 500 mM. It is preferred that the aqueous solution comprises as compound A a compound selected from the group polyalkylene glycol, polypropylene glycol, propylene glycol, polyethylene glycol, ethylene glycol, glycerol and mixtures thereof, more preferred a compound selected from polypropylene glycol, propylene glycol, polyethylene glycol, ethylene glycol and most preferred ethylene glycol.

The aqueous solution according to the present invention preferably does not contain dithiothreitol. Further preferred the aqueous solution according to the present invention does not contain β-mercapto-ethanol.

In a further preferred embodiment the pH of the aqueous solution is adjusted in the range of 5.6 to 9.6, preferably in the range of 6.0 to 9.0, further preferred in the range of 6.5 to 8.0 and most preferred in the range of 6.8 to 7.4.

A particularly preferred embodiment of the aqueous solution is having the capability of reducing unspecific binding, cross-reactivity and disturbing is effects of the matrix. The aqueous solution according to the present invention particularly has the capability of preventing the low-affinity binding with $K_D$ values of up to $10^{-7}$ M, compared to standard conditions. Further preferred the aqueous solution has the capability of preventing the low-affinity binding with $K_D$ values of up to $10^{-7}$ M and reducing the mid-range affinity binding with $K_D$ values in the range of between $10^{-7}$ M and $10^{-8}$ M by at least 90% compared to standard conditions. Even further preferred, the aqueous solution has the capability of preventing the low-affinity binding with $K_D$ values of up to $10^{-7}$ and reducing the mid-range affinity binding with $K_D$ values in the range of between $10^{-7}$ and $10^{-9}$ by at least 90% compared to standard conditions. As used herein "standard conditions" are represented by an aqueous solution consisting of 50 mM PBS (phosphate buffered saline, pH 7.4), 150 mM NaCl, 1% (w/v) BSA (see also table 1: reference example). The same results were obtained when comparing the measurements with another standard solution, namely an aqueous solution consisting of 50 mM PBS (pH 7.4), 100 mM NaCl, 0.05% (v/v) Tween®20.

Apart from the effect of reducing the unspecific, low affinity binding as well as matrix effects, the aqueous solution particularly preferred is having the capability to increase the binding activity of antibodies, preferably the binding activity of immobilized antibodies as well as the binding activity between ligands and receptors. The increase of the binding activity of immobilized antibodies by using the solution according to the present invention was about 10% or more.

The object of the present invention is also solved by a concentrate of the aqueous solution of the present invention desribed before, preferably a 2 to 10 fold concentrate, more preferred a 3 to 5 fold concentrate.

Further, the object of the present invention is solved by the use of the aqueous solution according to the present invention as a medium for the binding reaction of a binding pair, wherein a first binding member specifically recognizes and binds its complementary second binding member. Preferably the aqueous solution is used as a medium for the antibody-antigen binding reaction and in an alternative embodiment the aqueous solution is used as a medium for the receptor-ligand binding reaction. In other preferred embodiments the aqueous solution is used as dilution buffer for samples, reagents, ligands, receptors, antigens, antibodies. The aqueous solution may also preferably be used as a washing buffer in immunoassays after the binding reaction was carried out.

The invention further provides a method for reducing unspecific binding and/or cross-reactivity and/or disturbing effects of matrices during a specific binding reaction of a binding pair, wherein a first binding member recognises its complementary second binding member, the method comprising the use of the aqueous solution of the present invention as medium for the specific binding reaction.

In another aspect of the invention the aqueous solution according to the present invention can be provided as a component of a kit. As used herein, the term "kit" means a collection of reagents and associated materials e.g. buffers, carrier comprising an immobilised binding member and reagents which are required to perform an assay. Therefore, the present invention provides a kit for detection by immunoassay of at least one analyte to be tested, wherein the analyte to be tested is a first binding member of a binding member pair, wherein the first binding member binds specifically to its complementary binding member, the kit comprising:
- a) a vessel containing an aqueous solution of the present invention;
- b) a carrier comprising the complementary binding member immobilised thereon to capture the analyte; and
- c) optionally, a reagent which immunologically recognises the analyte bound to the complementary binding member, wherein the reagent (antibody) is conjugated to a means of detection; and
- d) optionally: reagents which are reactive with said means of detection to produce a detectable reaction product.

A typical kit for example is used as ELISA kit for the detection of, for example, antibodies in blood serum. In this case the carrier according to b) comprises as complementary binding member immobilised thereon, for example, a virus antigen to capture the analyte. The analyte which is the antibody in the blood serum. The reagent according to c) which immunologically recognises the analyte then is an anti-antibody which is recognising the captured antibody.

BEST MODE FOR CARRYING OUT THE INVENTION

The present invention is characterized in that the aqueous solution or use as medium for the specific binding reaction of a binding member pair, herein a first binding member recognizes its complementary second binding member, comprises:
- a) a buffer to control pH;
- b) a compound A selected from the group consisting of:
  a compound defined by the general formula I $R^1$—$[[CR^2R^3]_p$—$O]_q$—$R^4$, wherein $R^1$ is hydrogen or hydroxy group, $R^2$ for each unit independently is hydrogen or hydroxy group, $R^3$ is hydrogen, methyl group, ethyl group, $R^4$ is hydrogen or alkyl group, p is an integer of from 2 to 10 and q is an integer of from 1 to 100, with the proviso that the compound at least carries two hydroxy groups;
  polyol;
  saccharide;
- c) a non-ionic detergent.

The method of the present invention for reducing unspecific binding and/or cross-reactivity and/or disturbing effects of matrices during a specific binding reaction of a binding pair, wherein a first binding member recognises its complementary second binding member, i.e. for a immunoassy, is characterized to comprise the use of the above aqueous solution.

Preferably an aqueous solution was found to be useful which comprises compound A in a concentration in the range of 2 to 7% (v/v) and a non-ionic detergent in the range of between 0.2 to 0.8% (v/v). Preferably the aqueous solution is having an ionic strength of 200 mM to 1 M, more preferred of 200 mM to 800 mM, particularly more preferred of 200 mM to 600 mM and most preferred of 250 mM to 500 mM. It is preferred that the aqueous solution comprises as compound A a compound selected from the group polyalkylene glycol, polypropylene glycol, propylene glycol, polyethylene glycol, ethylene glycol, glycerol and mixtures thereof, more preferred a compound selected from polypropylene glycol, propylene glycol, polyethylene glycol, ethylene glycol and most preferred ethylene glycol.

The present inventions will be explained in more detail in the following examples. However, the examples are only used for illustration and do not limit the scope of the present invention.

EXAMPLES

Example 1

Reduction of Matrix Effects

100 µl diluted capture antibody C2 (final concentration 1 µg/ml in PBS-Buffer) was added to each well of a microtiter plate (C8 StarWell Module, NUNC) and the plate was covered with a plate sealer. The capture antibody is directed against CRP (c-reactive protein). Then the plate was incubated for 5 hours at room temperature. The plate sealer was removed and the plate was washed 4 times with 300 µl washing buffer (10 mM Phosphate, 350 mM NaCl, 0.05% Tween, pH 7.4) per well. Then 200 µl of blocking solution (PBS-Buffer pH 7.4, 1% BSA) was added to each well. After covering with a plate sealer the plate was incubated overnight at 4° C. The analyte CRP (c-reactive protein) was diluted in rabbit serum (0-5 ng/ml) and incubated for 30 min at room temperature. The biotin-labelled detector antibody C6 (directed against CRP) was diluted in different sample buffers and reference example buffers (see table 1). The final concentration was 4 µg/ml in each preparation. The CRP-containing rabbit serum standards were diluted 1:2 with detector antibody containing sample buffers. The preparations were incubated for 30 min at room temperature. The plate sealer was removed and the plate was washed 4 times with 300 µl washing buffer. Oddments of washing buffer were completely removed by taping the plate dry. 100 µl of the CRP-preparations were added to the wells. The plate was covered with a plate sealer and incubated for 4 h at room temperature under gentle shaking. After that the plate was washed again. 100 µl of diluted NeutrAvidin™-Horseradish peroxidase conjugated (final concentration 0.05 µg/ml in PBS-Buffer) was added to each well. The plate was incubated for 1 h at room temperature under gentle shaking. Then the plate was washed again. Equal volumes of the two solutions of ImmunoPure®TMB Substrat were mixed and 100 µl were added immediately to each well. The plate was incubated at room temperature until the desired colour developed. The colour changed from clear to brilliant blue. In a final step the reaction was stopped by adding 150 µl 2 M $H_2SO_4$ to each well and the absorbance was read out at 450 nm with an ELISA plate reader (Molecular devices). The influence of different buffers on matrix effects are plotted in FIG. 1. Table 1 shows the results of the test. In table 1 the reduction of non-specific binding, low-affinity binding and matrix effects is indicated in the column "result" with "+". The number of "+" is indicating the amount of reduction of non-specific binding, low-affinity binding and matrix effects compared to the reference example buffer ("−"). FIG. 1 shows the amount of detector antibody C6 bound to CRP as absorbance at 450 nm plotted against the concentration of CRP [ng/ml]. Sample buffer I shows the best sensitivity. The low sensitivity of the reference buffer is caused by a strong matrix effect.

Example 2

Reduction of an Unspecific Binding of a Polyclonal Detector Antibody

Figure 2:
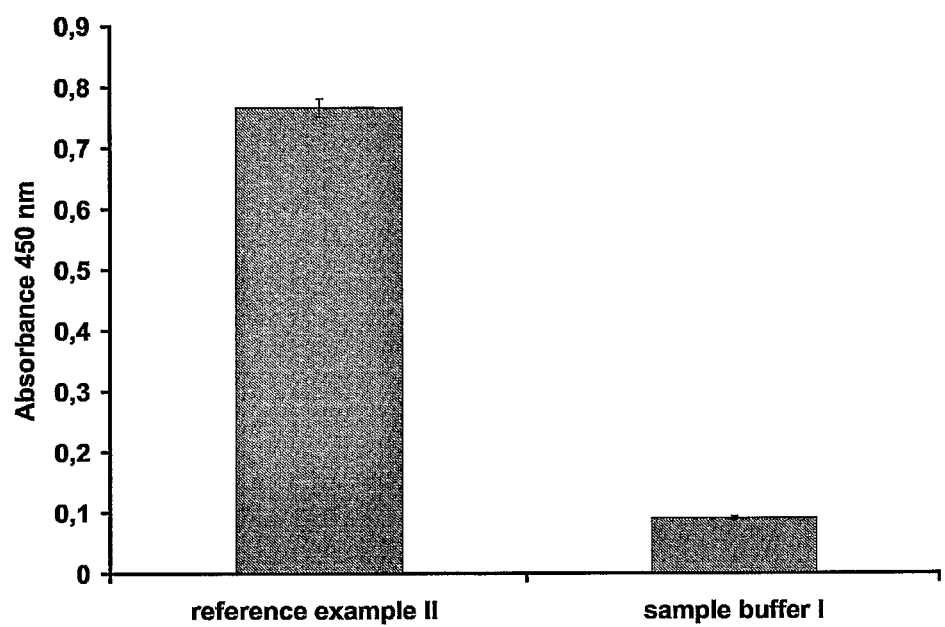
FIG. 2 shows the influence of two different buffers on high background signals caused by unspecific binding of the polyclonal detector antibody P2 which binds unspecific to the capture antibody P3 (according to Example 2). In this experiment no analyte was present. Sample buffer I decreases significantly the unspecific binding compared to the high background signals with reference example buffer II.

For the next assay 250 µl diluted capture antibody P3 (polyclonal rabbit-anti-protease, own preparation, final concentration 1 g/ml in PBS-Buffer) was added to each well of a microtiter plate (C8 StarWell Module, NUNC) and the plate was covered with a plate sealer. The plate was incubated for 4 hours at room temperature. After that the plate sealer was removed and the plate was washed 4 times with 300 µl washing buffer (10 mM Phosphate, 350 mM NaCl, 0.05% Tween®, pH 7.4) per well. Then 200 µl of blocking solution (PBS-Buffer pH 7.4, 1% BSA) was added to each well. The plate was covered again with a plate sealer and incubated overnight at 4° C. The biotin-labelled polyclonal detector antibody P2 (polyclonal rabbit-anti-protease, own preparation) was diluted in reference example buffer II or in sample buffer I (see table 1) respectively (final concentration 10 µg/ml in each preparation) and added to the wells (250 µl per well; fivefold replicates). The plate was incubated for 2 h at room temperature. The plate sealer was removed and the plate which binds unspecifically to the capture antibody P3 is plotted in FIG. 2. FIG. 2 shows the reduction of background signals due to the use of sample buffer I according to the present invention. In this experiment no analyte was used. Further, as antibody a polyclonal serum was used. A polyclonal serum comprises many different antibodies directed against a target protein. Many antibodies will bind with low or lower affinity, while some antibodies will bind with mid-range affinity and one or only a few antibodies will bind with high affinity. The use of the buffer according to the invention prevents the low-affinity binding and at least reduces the mid-range affinity binding of the respective antibodies as shown in FIG. 2. As a result, once an analyte will be added in such an assay the signal-to noise-ratio will be improved due to the properties of the aqueous solution according to the present invention.

TABLE 1

The table shows the results of the test according to Example 1: Result (=Reduction of non-specific, low-affinity binding and matrix effects)

| solution | Buffer/pH | Compound A [concentration] | Non-ionic detergent [concentration] | NaCl | BSA | Result |
|---|---|---|---|---|---|---|
| reference example (state of art) | PBS pH 7.4 | — | — | 150 mM | 1% | − |
| sample buffer I | Tris pH 7.4 | 5% ethylene glycol | 0.25 Tween ®20 | 300 mM | 1% | ++++ |
| sample buffer II | Tris pH 7.4 | 0.5% ethylene glycol | 0.1 Tween ®20 | 150 mM | 1% | + |
| sample buffer III | PBS pH 7.4 | 3% glycerol | 0.15 Triton X100 | 200 mM | 1% | ++ |
| sample buffer IV | Tris pH 7.4 | 5% glycerol | 0.25 Triton X100 | 300 mM | 1% | ++++ |
| sample buffer V | PBS pH 7.4 | 3% glycerol | 0.15 Triton X100 | 600 mM | 1% | +++ |
| reference example II (state of art) | PBS pH 7.4 | — | 0.05 Tween ®20 | 150 mM | 1% | −/+ |
| sample buffer VI | Tris pH 7.4 | 5% ethylene glycol | 0.25 Tween ®20 | — | — | +++ |
| sample buffer VII | Tris pH 7.4 | 5% polyethylene glycol | 0.25 Tween ®20 | — | — | +++ |
| sample buffer VIII | Tris pH 7.4 | 5% polypropylene glycol | 0.25 Tween ®20 | — | — | +++ |
| sample buffer IX | Tris pH 7.4 | 5% polyethylene glycol | 0.25 Tween ®20 | 300 mM | — | ++++ |
| sample buffer X | Tris pH 7.4 | 5% polypropylene glycol | 0.25 Tween ®20 | 300 mM | — | ++++ |
| sample buffer XI | Tris pH 7.4 | 5% polyethylene glycol | 0.25 Tween ®20 | 300 mM | 1% | ++++ |
| sample buffer XII | Tris pH 7.4 | 5% polypropylene glycol | 0.25 Tween ®20 | 300 mM | 1% | ++++ |
| sample buffer XIII | Tris pH 7.4 | 5% propylene glycol | 0.25 Tween ®20 | — | — | +++ |
| sample buffer XIV | Tris pH 7.4 | 5% propylene glycol | 0.25 Tween ®20 | 300 mM | — | ++++ |
| sample buffer XV | Tris pH 7.4 | 5% propylene glycol | 0.25 Tween ®20 | 300 mM | 1% | ++++ |
| sample buffer XVI | PBS pH 7.4 | 5% ethylene glycol | 0.25 Triton X100 | — | — | +++ |
| sample buffer XVII | PBS pH 7.4 | 5% ethylene glycol | 0.25 Triton X100 | 300 mM | — | ++++ |
| sample buffer XVIII | PBS pH 7.4 | 5% ethylene glycol | 0.25 Triton X100 | 300 mM | 1% | ++++ |
| sample buffer XIX | PBS pH 7.4 | 5% glycerol | 0.25 Triton X100 | — | — | + |
| sample buffer XX | PBS pH 7.4 | 5% glycerol | 0.25 Triton X100 | 300 mM | — | +++ |
| sample buffer XXI | PBS pH 7.4 | 5% glycerol | 0.25 Triton X100 | 300 mM | 1% | +++ |
| sample buffer XXII | PBS pH 7.4 | 5% trehalose | 0.25 Triton X100 | — | — | + |
| sample buffer XXIII | PBS pH 7.4 | 5% trehalose | 0.25 Triton X100 | 300 mM | — | ++ |
| sample buffer XXIV | PBS pH 7.4 | 5% trehalose | 0.25 Triton X100 | 300 mM | 1% | ++ | was washed 4 times with 300 µl washing buffer. Oddments of washing buffer were completely removed by taping the plate dry. 250 µl of diluted NeutrAvidin™-Horseradish peroxidase conjugated (final concentration 0.5 µg/ml in PBS-Buffer) was added to each well. The plate was incubated for 1 h at room temperature under gentle shaking. Then the plate was washed again. Equal volumes of the two solutions of ImmunoPure®TMB Substrat were mixed and 100 µl were added immediately to each well. The plate was Incubated at room temperature until the desired colour develops. The colour changes from clear to brilliant blue. In a final step the reaction was stopped by adding 150 µl 2 M $H_2SO_4$ to each well and the absorbance was read out at 450 nm with an ELISA plate reader (Molecular devices). The influence of the two different buffers on high background signals caused by unspecific binding of the polyclonal detector antibody P2

The invention claimed is:

1. A method for identifying the presence of an antigen or an antibody in a sample from a human subject, the method comprising:

contacting the sample with a complementary capture antibody or a capture antigen in an aqueous solution, specifically binding the antigen or the antibody to the complementary capture antibody or capture antigen, respectively; and detecting the presence of the antigen or antibody bound to the complementary capture antibody or capture antigen with a detector antibody that binds to either (a) the antigen, which is bound to the complementary capture antibody, or (b) the antibody, which is bound to the capture antigen, said sample further comprising a human anti-animal antibody that interferes with the specific binding between the antigen or the antibody in the sample and the complementary capture antibody or capture antigen, said aqueous solution comprising:
a) a buffer to control pH;
b) a compound A selected from the group consisting of polyalkylene glycol, polypropylene glycol, propylene glycol, polyethylene glycol, ethylene glycol, monosaccharides, disaccharides, trisaccharides, saccharose, mannose, trehalose, polyol, glycerol and mixtures thereof; and
c) a non-ionic detergent,
wherein the concentration of compound A is from 2.0-15.0% and the concentration of the non-ionic detergent is from 0.1-1.0%, wherein the concentration of compound A is in terms of % (v/v) when compound A is a liquid or the concentration of compound A is in terms of % (w/v) when compound A is a solid;
wherein the ratio of the non-ionic detergent to the compound A is from 1:15 to 1:25;
wherein the non-ionic detergent is a compound selected from the group consisting of:
a) a substituted phenyl residue having substituents $R^1$ and $R^2$ ($R^1$-Ph-$R^2$), wherein $R^1$ is $C_1$-$C_9$ alkyl group, $R^2$ is a —O—[$CH_2$—$CH_2$—O]$_a$—H group, wherein "a" is an integer of 5-40, wherein $R^2$ in respect to $R^1$ is para, meta or ortho position;
b)

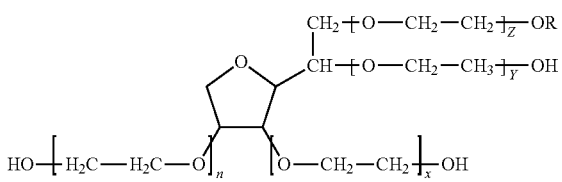

wherein n, x, y and z together is an integer of 5 to 40, R is a fatty acid residue;
c) Dodecylpoly(ethyleneglycolether)$_m$, wherein m is an integer of 5 to 40;
d) 1-O-n-Octyl-β-D-glucopyranodise (n-octylglucoside); and
e) 1-O-n-Dodecyl-β-D-glucopyranosyl (1-4)alpha-D-glucopyranoside; and
wherein said aqueous solution reduces the binding of the human anti-animal antibody in the sample to the complementary capture antigen or capture antibody, thereby reducing interference by the human anti-animal antibody with the specific binding of said antigen or antibody to the complementary capture antibody or capture antigen, compared to conducting said specific binding in the absence of said aqueous solution.

2. The method of claim 1, wherein said aqueous solution further comprises a protein in an amount effective to immunologically block non-specific antibody binding.

3. The method of claim 2, wherein the protein is selected from the group consisting of bovine serum albumin, ovalbumin, casein, and fetal bovine serum.

4. The method of claim 2, wherein the concentration of the protein is in the range of 0.1 to 2% w/v.

5. The method of claim 1, wherein the solution comprises a salt selected from the group consisting of NaCl, KCl, and $NH_4Cl$.

6. The method of claim 1, wherein the solution has an ionic strength of 100 mM to 1.5 M.

7. The method of claim 1, wherein the buffer is selected from the group consisting of Tris (Tris(hydroxymethyl)-aminomethane, Pipes (piperazine-1,4-bis-2-ethane sulfonic acid), Mes (4-Morpholino ethane sulfonic acid), Hepes (4-(2-hydroxyethyl)-1-piperazine-ethane sulfonic acid), and phosphate buffer.

8. The method of claim 1, wherein the non-ionic detergent is selected from the group consisting of alkylphenolpoly(ethylene-glycolether)$_m$, wherein m is an integer of 5 to 40; Dodecylpoly(ethyleneglycolether)$_m$, wherein m=23 (Brij35®); Poly(oxyethylene)(20)-sorbitane mono fatty acid ester; Poly(oxyethylene)(20)-sorbitane monooleate (Tween®80); Poly(oxyethylene)(20)-sorbitane monolaurate (Tween®20); Poly(oxyethylene)(20)-sorbitane monopalmitate (Tween®40); Poly(oxyethylene)(20)-sorbitane monostearate); and Octylphenolpoly(ethylene-glycolether)$_m$, wherein m is an integer of 5 to 40.

9. The method of claim 1, wherein the aqueous solution does not contain dithiothreitol.

10. The method of claim 1, wherein the pH is adjusted in the range of 5.6 to 9.6.

11. The method of claim 1, wherein the aqueous solution has the capability of preventing binding of human anti-animal with $K_D$ values of up to $10^{-7}$ M.

12. The method of claim 1, wherein the aqueous solution has the capability of preventing binding of human anti-animal with $K_D$ values of up to $10^{-7}$ M and reducing the mid-range affinity binding with $K_D$ values in the range of between $10^{-7}$ M and $10^{-8}$ M by at least 90%.

13. The method of claim 1, wherein the aqueous solution has the capability of preventing binding of human anti-animal with $K_D$ values of up to $10^{-7}$ M and reducing the mid-range affinity binding with $K_D$ values in the range of between $10^{-7}$ and $10^{-9}$ by at least 90%.

14. The method of claim 1, wherein said binding pair is an antibody-antigen binding pair.

15. The method of claim 1, wherein said binding pair is a receptor-ligand binding pair.

16. The method of claim 1, wherein said human anti-animal antibody is a human anti-mouse antibody.

17. The method of claim 8, wherein the non-ionic detergent is selected from the group consisting of Alkylphenolpoly(ethylene-glycolether)$_m$, wherein m=11 (Nonidet P40®); and Octylphenolpoly(ethylene-glycolether)$_m$, wherein m=10 (Triton®X 100).

* * * * *

UNITED STATES PATENT AND TRADEMARK OFFICE
CERTIFICATE OF CORRECTION

PATENT NO. : 8,877,514 B2  
APPLICATION NO. : 10/590686  
DATED : November 4, 2014  
INVENTOR(S) : Peter Rauch Page 1 of 1

It is certified that error appears in the above-identified patent and that said Letters Patent is hereby corrected as shown below:

In the Specification:

In column 1 at line 31, Change "extend" to --extent--.

In column 1 at line 58, Change "dilutents" to --diluents--.

In column 2 at line 11 (approx.), Change "immuno-sorbant" to --immuno-sorbent--.

In column 3 at line 39, Change "fluorophor" to --fluorophore--.

In column 3 at line 40, Change "Fluorophor-labled" to --Fluorophore-labeled--.

In column 4 at line 42, Change "cross-reactivies," to --cross-reactivities,--.

In column 4 at line 62, Change "coumpound" to --compound--.

In column 5 at line 6, Change "b" to --b)--.

In column 5 at line 39, Change "preferrred" to --preferred--.

In column 6 at line 9, After "disturbing" delete "is".

In column 6 at line 40, Change "desribed" to --described--.

In column 7 at line 30, Change "or" to --for--.

In column 7 at line 31, Change "herein" to --wherein--.

In column 7 at line 51, Change "immunoassy," to --immunoassay,--.

In the Claims:

In column 11 at line 43, In Claim 1, change "glucopyranodise" to --glucopyranoside--.

In column 12 at line 13 (approx.), In Claim 7, change "(piperazine" to --(Piperazine--.

Signed and Sealed this  
Fourth Day of August, 2015

Michelle K. Lee  
*Director of the United States Patent and Trademark Office*